US012692461B2

(12) United States Patent
Yaqoob et al.

(10) Patent No.: US 12,692,461 B2
(45) Date of Patent: Jul. 28, 2026

(54) COMPOSITE FORM OF TETRAACETYLENEDIAMINE

(71) Applicant: ONE1STAR SOLUTIONS LIMITED, North Yorkshire (GB)

(72) Inventors: Mohammed Yaqoob, West Yorkshire (GB); Samaira Yaqoob, West Yorkshire (GB)

(73) Assignee: ONE1STAR SOLUTIONS LIMITED, North Yorkshire (GB)

( * ) Notice: Subject to any disclaimer, the term of this patent is extended or adjusted under 35 U.S.C. 154(b) by 293 days.

(21) Appl. No.: 18/025,043

(22) PCT Filed: Sep. 8, 2021

(86) PCT No.: PCT/GB2021/052321

§ 371 (c)(1),
(2) Date: Mar. 7, 2023

(87) PCT Pub. No.: WO2022/053804

PCT Pub. Date: Mar. 12, 2022

(65) Prior Publication Data

US 2023/0313072 A1 Oct. 5, 2023

(30) Foreign Application Priority Data

Sep. 8, 2020 (GB) ...................................... 2014070

(51) Int. Cl.

| | |
|---|---|
| ***C11D 3/00*** | (2006.01) |
| ***C07C 233/36*** | (2006.01) |
| ***C11D 3/32*** | (2006.01) |
| ***C11D 3/39*** | (2006.01) |
| ***C11D 3/43*** | (2006.01) |

(Continued)

(52) U.S. Cl.
CPC .............. *C11D 3/32* (2013.01); *C07C 233/36* (2013.01); *C11D 3/3945* (2013.01); *C11D 3/43* (2013.01); *C11D 11/0082* (2013.01); *C11D 17/06* (2013.01); *C07B 2200/13* (2013.01)

(58) Field of Classification Search
CPC ........... C11D 3/32; C11D 3/3945; C11D 3/43; C11D 11/0082; C11D 17/06; C11D 3/39; C07C 233/36; C07B 2200/13
USPC .................................................. 510/372, 375
See application file for complete search history.

(56) References Cited

U.S. PATENT DOCUMENTS

| | | | | |
|---|---|---|---|---|
| 2010/0196505 | A1 | 8/2010 | Kaiser et al. | |
| 2016/0376522 | A1* | 12/2016 | Bianchetti et al. | A61Q 15/00 424/65 |

FOREIGN PATENT DOCUMENTS

| | | | | |
|---|---|---|---|---|
| CN | 108048251 | A | 5/2018 | |
| JP | 2004501880 | A * | 1/2004 | C07C 29/16 |
| JP | 2017-528569 | A | 9/2017 | |

(Continued)

OTHER PUBLICATIONS

Eurasian Office Action issued on Aug. 29, 2024 for Eurasian patent application No. 202390823 (filed on Sep. 8, 2021).

*Primary Examiner* — Eisa B Elhilo
(74) *Attorney, Agent, or Firm* — E. Eric Mills; Nicholas P. Stadnyk; Maynard Nexsen PC

(57) ABSTRACT

The present invention relates to a composite form of tetraacetylethylenediamine (TAED) and a method for its preparation. The composite form may comprise a new crystalline form. The invention also relates to the crystalline form itself. The present invention also relates to compositions comprising tetraacetylethylenediamine in these forms.

24 Claims, 2 Drawing Sheets

(51) Int. Cl.
*C11D 11/00* (2006.01)
*C11D 17/06* (2006.01)

(56) References Cited

FOREIGN PATENT DOCUMENTS

| | | | | | |
|---|---|---|---|---|---|
| JP | 2019-512575 | A | | 5/2019 | |
| JP | 2020132529 | A | | 8/2020 | |
| WO | 9618297 | A1 | | 6/1996 | |
| WO | WO 2017068348 | A1 | * | 4/2017 | ........... C07C 233/36 |
| WO | 2022/053784 | A1 | | 3/2022 | |

* cited by examiner

COMPOSITE FORM OF TETRAACETYLENEDIAMINE

CROSS REFERENCE TO RELATED APPLICATIONS

This application is a 35 U.S.C. § 371 U.S. national phase entry of International Application No. PCT/GB2021/052321 having an international filing date of Sep. 8, 2021, which claims the benefit of Great Britain Application No. 2014070.3 filed Sep. 8, 2021, each of which is incorporated herein by reference in its entirety.

The present invention relates to a composite form of tetraacetylethylenediamine (TAED) and a method for its preparation. The composite form may comprise a new crystalline form. The invention also relates to the crystalline form itself. The present invention also relates to compositions comprising tetraacetylethylenediamine in these forms.

BACKGROUND

Tetraacetylethylenediamine (TAED; IUPAC name: N,N'10 ethylenebis(diacetamide)); CAS registry number: 10543-57-4) is a well-known bleach activator which is mainly used in solid detergents or additives for laundry washing and dishwashing.

Two crystalline forms of TAED are known, form I and form II. Form I has very low solubility (0.2 g/litre at 20° C.) and a low dissolution rate in water.

It is an aim of certain embodiments of this invention to provide a stable form, e.g. a stable crystalline form, of TAED. It is an aim of certain embodiments of this invention to provide a form, e.g. a crystalline form, of TAED that is more stable than other forms.

It is an aim of certain embodiments of this invention to provide a form, e.g. a crystalline form, of TAED that is more soluble than other forms, e.g. other crystalline forms.

Certain embodiments of this invention satisfy some or all of the above aims.

BRIEF SUMMARY OF THE DISCLOSURE

In a first aspect of the invention is provided a composite form of tetraacetylethylenediamine (TAED), said composite form comprising TAED and an ionic component, wherein said ionic component is selected from a Deep Eutectic Solvent (DES), an Ionic liquid (IL) or a mixture thereof.

The TAED in the composite forms of the invention typically has a solubility greater than or equal about 2 g/L (calculated by mass of TAED present in the composite) at 20° C. Marketed TAED typically has a solubility around 200 mg/L. Similarly, in the presence of a bleaching agent, e.g. sodium percarbonate, the solubility of the TAED in the composite forms of the invention is typically considerably higher (around 4 g/L) than for marketed forms at 20° C. Thus, the composite forms of the invention are able to generate peracetic acid at high concentrations in water when in contact with an appropriate bleaching agent.

The composite form may be a gel. In this embodiment, the TAED will be the solid component of the gel and the ionic component will be the liquid component of the gel. The TAED may be dispersed in a liquid composed of the ionic component.

The composite form may be a solid. The TAED may be encapsulated in a solid of the ionic component. The TAED may be in admixture with the ionic component.

The composite form may comprise a surfactant. Said surfactant may be a solid surfactant. Typically, a composite form that comprises a solid surfactant will be a solid. The solid surfactant may be in admixture with the TAED and the ionic component.

Where a surfactant is present, it may be present in an amount from 10% w/w to 80% w/w by total weight of the composite form.

The TAED in the composite may be in crystalline form III.

Said composite form may be characterised in that said form is obtainable (e.g. obtained) by:

a) heating TAED with deep eutectic solvent (DES) forming components, a DES solvent (DES), an Ionic liquid (IL) or a mixture thereof to a temperature 150° C.;
b) allowing the mixture to cool to form the composite form.

The molar ratio of TAED to the ionic component may be in the range 3:1 to 1:3. The molar ratio of TAED to the ionic component may be in the range 2:1 to 1:2. The molar ratio of TAED to the ionic component may be about 1:1.

The TAED may be present in greater than 10% by total weight of the sum of the weights of the TAED and the ionic component. The TAED may be present in greater than 25% by total weight of the sum of the weights of the TAED and the ionic component. The TAED may be present in greater than 50% by total weight of the sum of the weights of the TAED and the ionic component. The TAED may be present in less than 95% by total weight of the sum of the weights of the TAED and the ionic component. The TAED may be present in less than 90% by total weight of the sum of the weights of the TAED and the ionic component. The TAED may be present in less than 80% by total weight of the sum of the weights of the TAED and the ionic component.

In a second aspect of the invention is provided a crystalline form of TAED, the crystalline form being form III.

The TAED in the composite form of the first aspect may be in the crystalline form of the second aspect.

Like the composite forms of the first aspect, TAED form III has a solubility and rate of solution which is considerably more than marketed TAED at 20° C. Thus, the TAED form III of the invention is able to generate peracetic acid at high concentrations in water when in contact with an appropriate bleaching agent.

Said crystalline form (i.e. Form III) may be characterised in that said form has an XRPD pattern having only two peaks at 2θ 9.1746±0.2 and 18.1788±0.2 when the crystalline form is dispersed in a DES solvent (DES), an Ionic liquid (IL) and wherein the XRPD is measured using Cu radiation with a $K_{\alpha 2}/K_{\alpha 1}$ ratio of 0.5.

For the absence of doubt, the two peaks are the only peaks in the XRPD pattern.

Said crystalline form (i.e. Form III) may be characterised in that said form is obtainable (e.g. obtained) by:

c) heating TAED with deep eutectic solvent (DES) forming components, a DES solvent (DES), an Ionic liquid (IL) or a mixture thereof to a temperature 150° C.;
d) allowing the mixture to cool to form TAED form III crystals dispersed in a DES or IL.

The TAED crystalline form III may be associated with the DES or IL. The TAED crystalline form III may be dispersed in liquid DES or IL. The TAED crystalline form III may be encapsulated in solid DES or IL.

It may be that said crystalline form has an XRPD pattern substantially as shown in FIG. 2.

In a third aspect of the invention is provided a method of forming a composite form of TAED, e.g. of the first aspect, the method comprising:

a) heating TAED with deep eutectic solvent (DES) forming components, a DES solvent (DES), an Ionic liquid (IL) or a mixture thereof to a temperature 150° C.; and
b) allowing the mixture to cool to form the composite form.

The method of the third aspect of the invention may be a method of forming the crystalline form of the second aspect of the invention, (e.g. the crystalline form form III), the method comprising:

c) heating TAED with deep eutectic solvent (DES) forming components, a DES solvent (DES), an Ionic liquid (IL) or a mixture thereof to a temperature 150° C.; and
d) allowing the mixture to cool to form TAED form III crystals dispersed in a DES or IL.

Where the TAED is heated with DES forming components, the product of step b will be solid TAED (e.g. TAED form III crystals) dispersed in a DES.

The temperature to which the mixture is heated in step a) may be 155° C. or greater. The temperature to which the mixture is heated in step a) may be 190° C. or less. The temperature to which the mixture is heated in step a) may be 175° C. or less.

The product of step b) has a gel like consistency the properties of which can be controlled by altering the identity of the DES or IL or mixture thereof. This gel like material can be solidified to form the TAED form III by addition of the additives like surfactants, polymers and other detergent based components. Viscosity of the product of step b) can range from highly viscous 1000 cP to 120000 cP.

The TAED may be heated with choline chloride and urea.

The molar ratio of choline chloride to urea may be in the range 1:1 to 4:1 (e.g. about 2:1).

The molar ratio of TAED to the DES (or DES forming components) or IL may be in the range 3:1 to 1:3. The molar ratio of TAED to the DES or IL may be in the range 2:1 to 1:2. The molar ratio of TAED to the DES or IL may be about 1:1.

Where the DES comprises choline chloride and urea, the molar ratio of TAED to choline chloride may be in the range 2:1 to 1:2. The molar ratio of TAED to the choline chloride may be about 1:1.

The TAED may be present in greater than 10% by total weight of the sum of the weights of the TAED and the ionic component. The TAED may be present in greater than 25% by total weight of the sum of the weights of the TAED and the ionic component. The TAED may be present in greater than 50% by total weight of the sum of the weights of the TAED and the ionic component. The TAED may be present in less than 95% by total weight of the sum of the weights of the TAED and the ionic component. The TAED may be present in less than 90% by total weight of the sum of the weights of the TAED and the ionic component. The TAED may be present in less than 80% by total weight of the sum of the weights of the TAED and the ionic component.

The TAED when heated with ionic liquid or with DES solvent at or above 150° C. or 155° C. gives clear liquid which upon cooling allow TAED to recrystallise into form III.

The stability of form III when dispersed in DES or IL is good. Where the product of step b) has a viscosity of 5000 cP, the dispersion has been shown to be physically and chemically stable for 6 months at 40° C. 75% RH stability conditions.

Thus, it may be that the eutectic solvent (DES) forming components, DES solvents (DES) or Ionic liquid (IL) are selected such that the liquid component of the product of step b) has a viscosity in the range from 5000 cP to 120000 cP.

The rate of solution of TAED in the DES or IL system can be further enhanced by addition of liquid additives such as propylene glycol (1,2-Propylene Glycol) or sodium tripolyphosphate, caustic soda, sulphonic acid etc or mixture of these components. Thus, the heating step a) may be conducted in the presence of propylene glycol (1,2-Propylene Glycol) or sodium tripolyphosphate, caustic soda, sulphonic acid or a mixture thereof.

The method may further comprise step c): adding a surfactant to the product of b) to cause the DES or IL to solidify, encapsulating the crystalline form III of TAED.

Said surfactant may be a solid surfactant.

Suitable solid surfactants include: Cresylic acid, Denatonium benzoate, Potassium peroxomonosulphate (KMPS), Glycollic acid, Sodium peroxodisulphate (NPS), Surface modifying polymers, Sodium sulphate, Zinc ricinoleate, Ethylene glycol distearate, Alkyl Polypentosides (APPs), Alkylpolyglucosides (APGs), Amine oxides, Amphoacetates, Cocamide DEA and MEA, Cocoaminopropionate, Cocoamphodipropionate, Cocoiminodipropionate, Didecyl dimethyl ammonium carbonate/bicarbonate, Dodecyl Benzene Sulfonic Acid (DDBSA), MEA & TEA neutralised DDBSA, Ethoxylated fatty amines, Fluorinated surfactants, Octyliminodipropionate, OXO alcohol ethoxylates, PEG-7 glyceryl cocoate, Propoxylate/Ethoxylates, Silicone surfactants, Sodium C14-16 Olefin Sulphonate (AOS), Sodium C14-17 Alkyl Sec-Sulphonate (SAS), Sodium Laureth Sulphate (SLES), Sodium Lauryl Sulphate (SLS), Urea.

The method of the third aspect may be a method of forming the composite form of the first aspect. The method of the third aspect may be a method of forming the crystalline form of the second aspect.

The composite form of the first aspect may be made according to the method of the third aspect. The crystalline form of the first aspect may be made according to the method of the third aspect.

In a fourth aspect of the invention is provided a composition comprising either a composite form of TAED of the first aspect or a crystalline form of TAED of the second aspect.

The composition may be a solid composition, e.g. a powder composition. The composition may be a suspension or paste in which the TAED composite form is present as a solid.

The composition may be a detergent composition. The composition may be a bleaching composition.

The composition may comprise from 0.1% to 20% by weight of crystalline form of TAED of the first aspect.

Typically the TAED form Ill will be encapsulated in solid DES or Ionic liquid.

The composition will typically also comprise a solid surfactant, e.g. a solid surfactant selected from Cresylic acid, Denatonium benzoate, Potassium peroxomonosulphate (KMPS), Glycollic acid, Sodium peroxodisulphate (NPS), Surface modifying polymers, Sodium sulphate, Zinc ricinoleate, Ethylene glycol distearate, Alkyl Polypentosides (APPs), Alkylpolyglucosides (APGs), Amine oxides, Amphoacetates, Cocamide DEA and MEA, Cocoaminopropionate, Cocoamphodipropionate, Cocoiminodipropionate, Didecyl dimethyl ammonium carbonate/bicarbonate, Dodecyl Benzene Sulfonic Acid (DDBSA), MEA & TEA neutralised DDBSA, Ethoxylated fatty amines, Fluorinated surfactants, Octyliminodipropionate, OXO alcohol ethoxylates, PEG-7 glyceryl cocoate, Propoxylate/Ethoxylates, Silicone surfactants, Sodium C14-16 Olefin Sulphonate (AOS), Sodium C14-17 Alkyl Sec-Sulphonate (SAS), Sodium Laureth Sulphate (SLES), Sodium Lauryl Sulphate (SLS), Urea.

The composition may comprise one or more additional bleach activators. The one or more additional bleach activators may be selected from the group comprising crystalline Form I of TAED, crystalline Form II of TAED, triacetylethylendiamine, nonanoyloxybenzene sulphonate (NOBS) and dodecanoyloxybenzene sulphonate (DOBS).

The composition may further comprise a bleaching agent. The bleaching agent may be a metal percarbonate salt. The bleaching agent may be an alkali metal percarbonate salt, e.g. sodium percarbonate or potassium percarbonate. The bleaching agent may be sodium percarbonate.

The composition may further comprise at least one of a surfactant or wetting agent. The composition may further comprise at least one of an additive selected from the group consisting of a pH modifier, a chelating agent, a stabilising agent, a diluent, a glidant, a binding agent, an effervescing agent, a disintegrating agent and a coating agent.

BRIEF DESCRIPTION OF THE DRAWINGS

Embodiments of the invention are further described hereinafter with reference to the accompanying drawings, in which.

DETAILED DESCRIPTION

Figure 1:
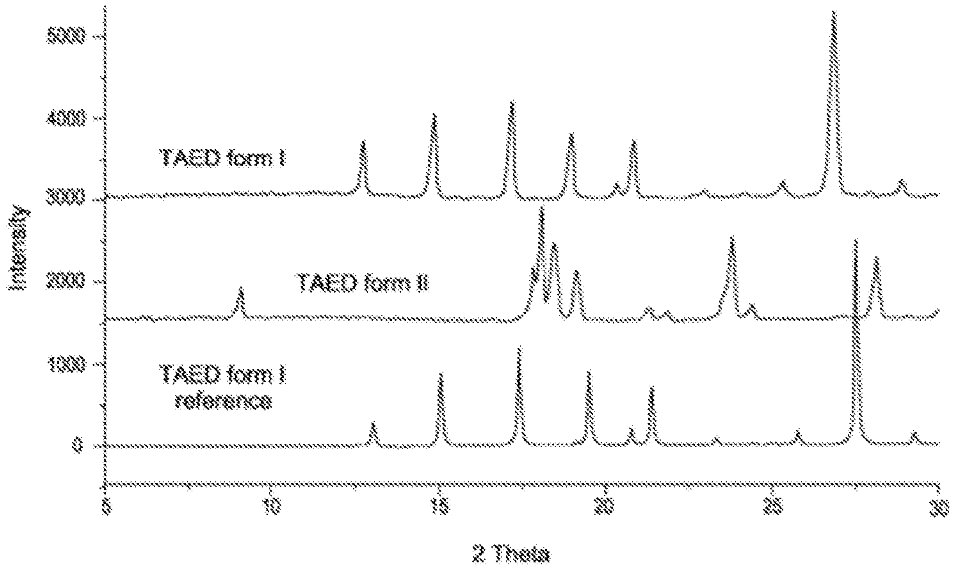
FIG. 1 shows the PXRD pattern for TAED Forms I and II (taken from WO2017068348A1).

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996)."

Deep Eutectic Solvents

Deep eutectic solvents are systems formed from a eutectic mixture of Lewis or Brönsted acids and bases which can contain a variety of anionic and/or cationic species. They are classified as types of ionic solvents with special properties. They incorporate one or more compound in a mixture form, to give a eutectic with a melting point much lower than either of the individual components. One of the most significant deep eutectic phenomenon was observed for a mixture of choline chloride and urea in a 1:2 mole ratio. The resulting mixture has a melting point of 12° C. (far less than the melting point of choline chloride, 302° C. and urea, 133° C.), which makes it liquid at room temperature.

The first generation eutectic solvents were based on mixtures of quaternary ammonium salts with hydrogen bond donors such as amines and carboxylic acids. There are four types of eutectic solvents:

Type I Quaternary ammonium salt+metal chloride

Type II Quaternary ammonium salt+metal chloride hydrate

Type III Quaternary ammonium salt+hydrogen bond donor

Type IV Metal chloride hydrate+hydrogen bond donor

Eutectic solvent further comprises: reacting an ammonium compound with a second compound selected from the group consisting of amines, amides, carboxylic acids, alcohols, metal halides, and combinations thereof.

Deep Eutectic Solvents or solution (DES) is formed by complexing an ammonium compound, for example N-(2-hydroxyethyl) trimethyl-ammonium chloride (choline chloride), with a hydrogen-bond donor (HBD) such as carboxylic acids, amines, amides and alcohols. These liquids have physical and solvent properties that are similar to ionic liquids formed from discrete ions and are easy to produce by simply mixing common commodity chemicals such as choline chloride and carboxylic acids or amides.

Other examples include: Choline chloride:lactic acid DES, and proline:lactic acid DES, Choline chloride:citric acid and dimethylurea:citric acid, propylene glycol:citric acid DES.

The ionic component may be a DES selected from choline chloride:lactic acid DES; and proline:lactic acid DES; choline chloride:citric acid DES and propylene glycol:citric acid DES. The ionic component may be propylene glycol:citric acid DES.

Ionic Liquids

Illustrative ionic liquids include those described in WO2006050307, US20190085273 and WO2017156141.

Illustrative Ionic Liquids Include:

imidazolium salts, such as 1-butyl-3-methylimidazolium hexafluorophosphate, also known as [bmim]. Other well known ionic liquids include 1-ethyl-3-methylimidazolium chloride-aluminium (III) chloride, which is usually referred to as [emim] Cl—$AlCl_3$; and N-butyl pyridinium chloride aluminium (III) chloride, which is usually referred to as [Nbupy] Cl—$AlCl_3$.

Another illustrative ionic liquid is diisopropanolamine (DIPA).

Nonlimiting examples of anions and cations suitable for use in the ionic liquids for the present invention are disclosed below.

Anions

Anions suitable for use in the ionic liquids of the present invention include, but are not limited to, the following materials:

(1) Alkyl sulfates (AS), alkoxy sulfates and alkyl alkoxy sulfates; nonlimiting examples of alkoxy sulfate include sulfated derivatives of commercially available alkoxy copolymers, such as Pluronics® (from BASF);

(2) Mono- and di-esters of sulfosuccinates: nonlimiting examples include saturated and unsaturated $C_{12-18}$ monoester sulfosuccinates, such as lauryl sulfosuccinate available as Mackanate LO-100® (from The McIntyre Group); saturated and unsaturated $C_6$-$C_{12}$ diester sulfosuccinates, such as dioctyl ester sulfosuccinate available as Aerosol OT® (from Cytec Industries, Inc.);

(3) Methyl ester sulfonates (MES);

(4) Alkyl aryl sulfonates, nonlimiting examples include tosylate, alkyl aryl sulfonates having linear or branched, saturated or unsaturated $C_8$-$C_{14}$ alkyls; alkyl benzene sulfonates (LAS) such as $C_{11}$-$C_{12}$ alkyl benzene sulfonates;

(5) Alkyl glycerol ether sulfonates having 8 to 22 carbon atoms in the alkyl moiety;

(6) Diphenyl ether (bis-phenyl) derivatives: Nonlimiting examples include triclosan (2,4,4'-trichloro-2'-hydroxydiphenyl ether) and diclosan (4,4'-dichloro-2-hydroxydiphenyl ether), both are available as Irgasan® from Ciba Specialty Chemicals;

(7) Linear or cyclic carboxylates: nonlimiting examples include Citrate, lactate, tartarate, succinate, alkylene succinate, maleate, gluconate, formate, cinnamate, benzoate, acetate, salicylate, phthalate, aspartate, adipate, acetyl salicylate, 3-methyl salicylate, 4-hydroxy isophthalate, di hydroxyfumarate, 1,2,4-benzene tricarboxylate, pentanoate and mixtures thereof;

(8) Mid-chain branched alkyl sulfates (HSAS), mid-chain branched alkyl aryl sulfonates (MLAS) and mid-chain branched alkyl polyoxyalkylene sulfates; nonlimiting examples of MLAS are disclosed in U.S. Pat. Nos. 6,596,680; 6,593,285; and 6,202,303;

(9) Sarcosinates; nonlimiting examples include ammonium lauroyl sarcosinate, available as Hamposyl AL-30® from Dow Chemicals and sodium oleoyl sarcosinate, available as Hamposyl O® from Dow Chemical;

(10) Sulfated and sulfonated oils and fatty acids, linear or branched, such as those sulfates or sulfonates derived from potassium coconut oil soap available as Norfox 11010 from Norman, Fox & Co. and Potassium oleate from Chemron Corp.;

(11) Fatty acid ester sulfonates;

(12) Sweetener derived anions: saccharinate and acesulfamate;

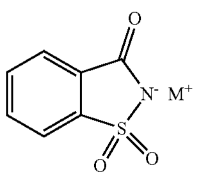

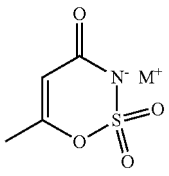

saccharinate acesulfamate wherein M+ is a cation selected from the cations of the ionic liquids described below;

(13) Ethoxylated amide sulfates; sodium tripolyphosphate (STPP); dihydrogen phosphate; fluroalkyl sulfonate; bis-(alkylsulfonyl)amine; bis-(fluoroalkylsulfonyl) amide; (fluroalkylsulfonyl)(fluoroallcylcarbonyl) amide; bis(arylsulfonyl)amide; carbonate; tetrafluoroborate ($BF4^-$); hexaflurophosphate ($PF6^-$);

(14) Anionic bleach activators, nonlimiting include such as:

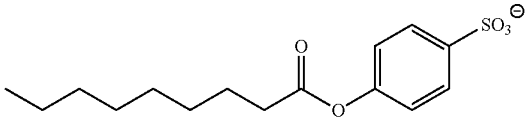

4-nonanoyloxybenzene sulfonate

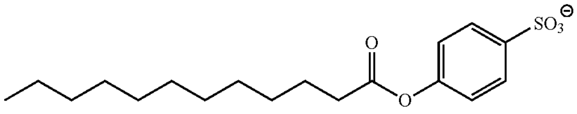

4-dodecanoyloxybenzene sulfonate

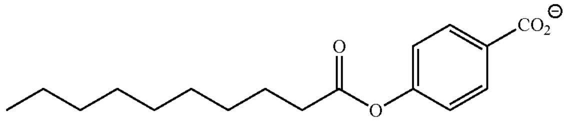

4-decanoyloxybenzoate are disclosed in U.S. Pat. Nos. 5,891,838; 6,448,430; 5,891,838; 6,159,919; 6,448,430; 5,843,879; 6,548,467.

Cations

Cations suitable for use in the ionic liquids of the present invention include, but are not limited to, the following materials:

(a) Cations (i.e., in the protonated, cationic form) of amine oxides, phosphine oxides, or sulfoxides;

(b) Betaines; nonlimiting examples of betaines include dodecyl dimethyl betaine, acetyl dimethyl betaine, dodecyl amidopropyl dimethyl betaine, tetradecyl dimethyl betaine, tetradecyl amidopropyl dimethyl betaine, dodecyl dimethyl ammonium hexanoate; and amidoalkylbetaines which are disclosed in U.S. Pat. Nos. 3,950,417; 4,137,191; and 4,375,421; and British Patent GB No. 2,103,236; in another embodiment, the cation may be a sulfobetaine, which are disclosed in U.S. Pat. No. 4,687,602;

(c) Diester quaternary ammonium (DEQA) cations e.g. the DEQA cations as discussed in U.S. Pat. No. 6,004,922 (d) Alkylene quaternary ammonium cations e.g.

dialkylenedimethyl ammonium cations, such as dioleyldimethyl ammonium available from Witco Corporation under the tradename Adogen® 472; or monoalkenyltrimethyl ammonium, such as monooleyltrimethyl ammonium, monocanolatrimethyl ammonium, and soyatrimethyl ammonium;

(e) Di-fatty amido quaternary ammonium cations for example, difatty amido quats are commercially available from Witco under the Varisoft® tradename;

(f) $C_{8-22}$ quaternary surfactants such as isostearyl ethyl imidonium available in its ethosulfate salt form as Schercoquat IIS® from Scher Chemicals, Inc., quaternium-52 obtainable as Dehyquart SP® from Cognis Corporation, and dicoco dimethyl ammonium available in its chloride salt form as Arquad 2C-75® from Akzo Nobel Surface Chemistry LLC;

(g) Cationic esters such as discussed in U.S. Pat. Nos. 4,228,042, 4,239,660, 4,260,529 and 6,022,844;

(h) 4,5-dichloro-2-n-octyl-3-isothiazolone, which is obtainable as Kathon® from Rohm and Haas;

(i) Quaternary amino polyoxyalkylene derivatives (choline and choline derivatives);

(j) Alkyl oxyalkylene cations;

(k) Alkoxylate quaternary ammoniums (AQA) as discussed in U.S. Pat. No. 6,136,769;

(l) Substituted and unsubstituted pyrrolidinium, imidazolium, benzimidazolium, pyrazolium, benzpyrazolium, thiazolium, benzthiazolium, oxazolium, benzoxazolium, isoxazolium, isothiazolium, imdazolidenium, Guanidinium, indazolium, quinuclidinium, triazolium, isoquinuclidinium, piperidinium, morpholinium, pyridazinium, pyrazinium, triazinium, azepinium, diazepinium, pyridinium, piperidonium, pyrimidinium, thiophenium; phosphonium;

(m) Cationic bleach activators having a quaternary ammonium moiety including but not limited to

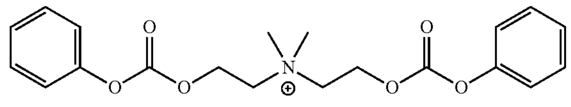 [SMILES: C[N+](C)(CCOC(=O)Oc1ccccc1)CCOC(=O)Oc1ccccc1]

N,N-dimethyl-2-[(phenoxycarbonyl)oxy]-N-[2-[(phenoxycarbonyl)oxy]ethyl]ethanaminium

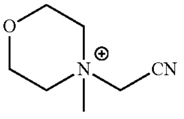

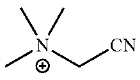

4-(cyanomethyl)-4-methylmorpholinium; 1-cyano-N,N,N-trimethylmethanaminium

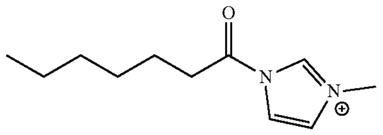

1-methyl-3-(1-oxoheptyl)-1H-Imidazolium these and other cationic bleach activators suitable for use herein as cations of the ionic liquids are disclosed in U.S. Pat. Nos. 5,599,781, 5,686,015, 5,686,015, WO 95/29160, U.S. Pat. Nos. 5,599,781, 5,534,179, EP 1 253 190 A1, U.S. Pat. Nos. 6,183,665, 5,106,528, 5,281,361, and Bulletin de la Societe Chimique de France (1973), (3)(Pt. 2), 1021-7;

(n) Cationic anti-microbial agents, such as cetyl pyridinium, chlorohexidine and domiphen.

(o) Alkylated caffeine cations.

Figure 2:
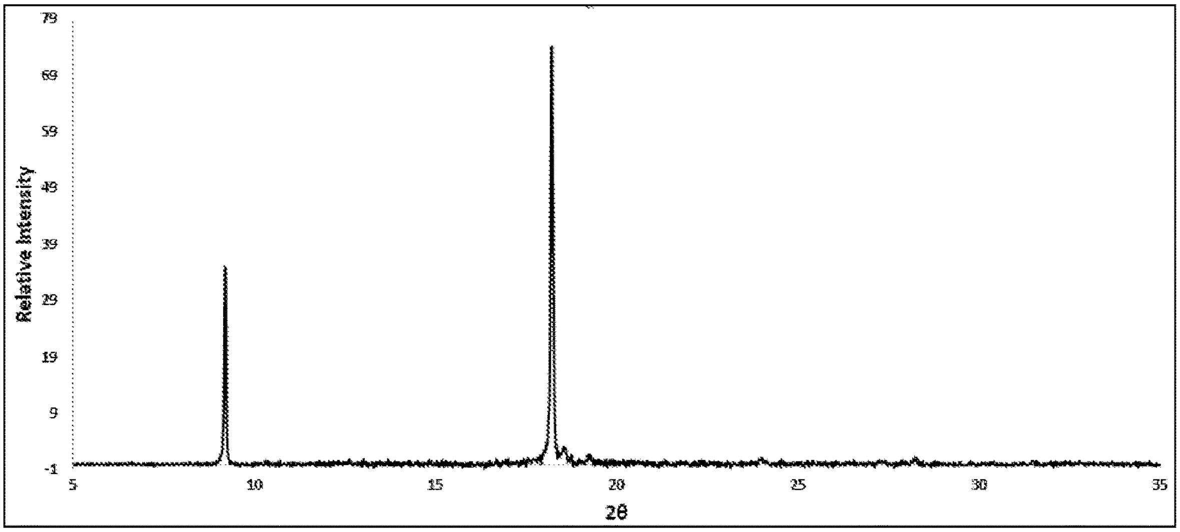
FIG. 2 shows the PXRD pattern for TAED Form III.

The invention may also be described according to the following numbered paragraphs:

1. A crystalline form of TAED (form 111), said crystalline form being characterised in that said form has an XRPD pattern having only two peaks at $2\theta$ 9.1746±0.2 and 18.1788±0.2 when the crystalline form is dispersed in a DES solvent (DES), an Ionic liquid (IL) and wherein the XRPD is measured using Cu radiation with a $K_{\alpha 2}/K_{\alpha 1}$ ratio of 0.5.
2. The crystalline form of paragraph 1, wherein said crystalline form has an XRPD pattern substantially as shown in FIG. 2.
3. A method of forming a crystalline form of TAED (Form III), the method comprising:
   a) heating the TAED with deep eutectic solvent (DES) forming components, a DES solvent (DES), an Ionic liquid (IL) or a mixture thereof to a temperature 150° C.; and
   b) allowing the mixture to cool to form TAED form III crystals dispersed in the DES or IL.
4. A method of paragraph 3, wherein the eutectic solvent (DES) forming components, DES solvents (DES) or Ionic liquid (IL) are selected such that the product of step b) has a viscosity in the range from 5000 cP to 120000 cP.
5. A method of paragraph 3, wherein TAED solubility in presence of sodium percarbonate to generate resultant highly concentrated peracetic acid system can be achieved (more than 4 gram TAED in 100 ml water)
6. A method of paragraph 3, wherein the eutectic solvent (DES) forming components, DES solvents (DES) or Ionic liquid (IL) are used to heat, melt and recrystallize TAED, which if converts from Form III to Form I, its rate of solution in water will not change over the period of time (water solubility will not change)
7. A method of paragraph 3 or paragraph 4, wherein the heating step a) may be conducted in the presence of propylene glycol (1,2-Propylene Glycol) or sodium tripolyphosphate, caustic soda, sulphonic acid or a mixture thereof.
8. A method of any one of paragraphs 3 to 5, wherein the method comprises step c): adding a solid surfactant to the product of b) to cause the DES or IL to solidify to provide crystalline form III of TAED encapsulated in DES or IL.
9. A method of paragraph 6, wherein the surfactant is selected from: Cresylic acid, Denatonium benzoate, Potassium peroxomonosulphate (KMPS), Glycollic acid, Sodium peroxodisulphate (NPS), Surface modifying polymers, Sodium sulphate, Zinc ricinoleate, Ethylene glycol distearate, Alkyl Polypentosides (APPs), Alkylpolyglucosides (APGs), Amine oxides, Amphoacetates, Cocamide DEA and MEA, Cocoaminopropionate, Cocoamphodipropionate, Cocoiminodipropionate, Didecyl dimethyl ammonium carbonate/bicarbonate, Dodecyl Benzene Sulfonic Acid (DDBSA), MEA & TEA neutralised DDBSA, Ethoxylated fatty amines, Fluorinated surfactants, Octyliminodipropionate, OXO alcohol ethoxylates, PEG-7 glyceryl cocoate, Propoxylate/Ethoxylates, Silicone surfactants, Sodium C14-16 Olefin Sulphonate (AOS), Sodium C14-17 Alkyl Sec-Sulphonate (SAS), Sodium Laureth Sulphate (SLES), Sodium Lauryl Sulphate (SLS), Urea and mixtures thereof.
10. A crystalline form of TAED (form Ill), said crystalline form being characterised in that it is obtainable by the method of any one of paragraphs 3 to 7.
11. A composition comprising the crystalline form of TAED of any one of paragraphs 1, 2 and 8.
12. A composition of paragraph 9, wherein the composition is a solid composition.
13. A composition of paragraph 9 or paragraph 10, wherein the TAED form III is encapsulated in solid DES or Ionic liquid.
14. A composition of any one of paragraphs 9 to 11, wherein the composition comprises from 0.1% to 20% or 0.1 to 50% or more 75% by weight of the crystalline form of TAED Form I of any one of paragraphs 1, 2 and 8.

15. A composition of any one of paragraphs 9 to 12, wherein the composition further comprises a solid surfactant.
16. A composition of paragraph 13, wherein the surfactant is selected from: Cresylic acid, Denatonium benzoate, Potassium peroxomonosulphate (KMPS), Glycollic acid, Sodium peroxodisulphate (NPS), Surface modifying polymers, Sodium sulphate, Zinc ricinoleate, Ethylene glycol distearate, Alkyl Polypentosides (APPs), Alkylpolyglucosides (APGs), Amine oxides, Amphoacetates, Cocamide DEA and MEA, Cocoaminopropionate, Cocoamphodipropionate, Cocoiminodipropionate, Didecyl dimethyl ammonium carbonate/bicarbonate, Dodecyl Benzene Sulfonic Acid (DDBSA), MEA & TEA neutralised DDBSA, Ethoxylated fatty amines, Fluorinated surfactants, Octyliminodipropionate, OXO alcohol ethoxylates, PEG-7 glyceryl cocoate, Propoxylate/Ethoxylates, Silicone surfactants, Sodium C14-16 Olefin Sulphonate (AOS), Sodium C14-17 Alkyl Sec-Sulphonate (SAS), Sodium Laureth Sulphate (SLES), Sodium Lauryl Sulphate (SLS), Urea and mixtures thereof.
17. A composition of any one of paragraphs 9 to 14, wherein the composition further comprises a bleaching agent.
18. A composition of any one of paragraphs 9 to 15, wherein the composition further comprises at least one of a surfactant or wetting agent.
19. A composition of any one of paragraphs 9 to 16, wherein the composition further comprises at least one of an additive selected from the group consisting of a pH modifier, a chelating agent, a stabilising agent, a diluent, a glidant, a binding agent, an effervescing agent, a disintegrating agent and a coating agent.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

General Procedures

Procedure I

Accurately weigh ionic liquid or DES forming components in molar proportion (for example, propylene glycol and citric acid in 1:2 OR 1:1 molar proportion) in a glass beaker Heat the mixture above 150° C. until clear liquid is obtained Add TAED to it and stir the mixture until clear liquid obtained Turn off the heating when clear liquid obtained Let the final mixture cool down. The TAED typically recrystallises to polymorphic Form III.

The PXRD of the mixture was done after complete cooling of the mixture to confirm the formation of TAED polymorphic form III

Procedure II

Weigh accurately the ionic liquid or DES forming components (for example propylene glycol:citric acid in 1:2 and 1:1 molar proportion) and add accurately needed amount of TAED to it Mix these components well Heat this mixture under stirring above 150° C.

Once clear liquid is obtained, turn of the heating and let the mixture cool down Do the PXRD of cooled mixture to confirm the TAED polymorphic form III

Example 1—Process for the Isolation of (S)-Epimer in Form Ill

Following Procedure II, take 1 gram of TAED, and DES forming components in equimolar ratio (for example propylene glycol:citric acid 1:2, take 0.76 gram propylene glycol and 3.84 gram of citric acid)

Mix all above ingredients and heat them in beaker above 150 C (155° C. or 160° C.) until it gives a liquid homogenous end product The end product should be cooled down

Example 2—X-Ray Powder Diffraction (XRPD)

The viscous sample of the crystalline form III of TAED suspended in the DES of Example 1 (TAED is 20% by total weight of composite. The DES is propylene glycol:citric acid in 1:1 molar ratio) was spread on the sample holder. PXRD patterns were analysed using instrument having X-ray wavelength 1.54 Å and a 40 KV Cu (Kα) source with filament emission 40 mA. All samples were scanned from 5 to 35° (2θ) using, a 0.01° step width and 1 s time count. A scatter slit and receiving slit were 0.2° and 1°.

The resulting spectrum is shown in FIG. 2. The observed peaks were as follows:

| No. | Pos. [°2Th.] | d-spacing [Å] | Rel. Int. [%] |
|---|---|---|---|
| 1 | 9.1746 | 9.63 | 46.97 |
| 2 | 18.1788 | 4.87 | 100 |

2Th.=° 2θ. Typically an error of ±0.2° 2θ is present in XRPD peak positions.

The inventors have also shown that crystalline form III of TAED is produced when Example 1 is repeated using choline chloride:lactic acid DES; proline:lactic acid DES; and choline chloride:citric acid DES. The inventors have also shown that crystalline form III of TAED is produced when Example 1 is repeated using diisopropanolamine ionic liquid.

Example 3: Procedure for Performance and Water Miscibility @20° C.

TAED when added to water in presence of sodium percarbonate gives peracetic acid, the rate of peracetic acid formation was compared using TAED form III in DES composite of the invention (TAED is 20% by total weight of composite. The DES is propylene glycol:citric acid in 1:1 molar ratio) and commercial TAED form I.

Experimental Details

The experiment was carried out to check the performance and water miscibility of TAED in presence of sodium percarbonate. 1 gram of TAED with 2.5 gram of sodium percarbonate was added 1 litre water and stirred at 500 rpm using overhead stirrer. In Experiment set up the amount of water used for the study was 1 litre. The weight of the remaining material after 5 min was calculated. Results shows that DES based form III shows complete miscibility or clear solution as compared to marketed TAED. Results are shown in Table below

TABLE 2

| Material | Time (5 min) |
|---|---|
| TAED (Commercially available) | 600 ± 10 mg (unclear turbid solution) |
| TAED composite of the invention | 0 mg (clear solution) |

The above result shows that how quickly TAED form III in DES/Ionic liquid goes into water in presence of sodium percarbonate to form peracetic acid. Similar studies were carried out with less amount of water 100 ml, 250 ml, 500 ml, all the studies gave similar results as above the amount remained after 5 min were less than 5-10 mg in case TAED DES system and commercial TAED remained was 800 mg in 100 ml study, whereas for 250 ml study TAED DES system solution was clear and similarly in 500 ml trials as well whereas commercial TAED remained was 750 mg and 690 mg respectively Similar studies were carried out where TAED amount was increased to 5 gram in 1 litre water results are shown in Table below

TABLE 3

| Material | Time (5 min) |
|---|---|
| TAED (Commercially available) | 4100 ± 10 mg (unclear turbid solution) |
| TAED composite of the invention | 0 ± 5 mg (clear solution) |

One study was carried out in such a way that maximum amount of TAED DES system (TAED amount was 4 gram in TAED DES system) in less amount of water i.e. 100 ml, after 5 min of stirring the solution started to get clear and after stirring continued further almost all the solution got cleared (Material remained after filtration of the final solution was less than 100 mg), this indicates the efficiency of TAED DES system for the solubility in water and highest amount of peracetic acid generation can be achieved using TAED DES system without heating and in water at room temperature.

The inventors have also shown that similar results are obtained with composites comprising choline chloride:lactic acid DES; proline:lactic acid DES; and choline chloride: citric acid DES; and diisopropanolamine ionic liquid.

Example 4

TAED when added to water in presence of sodium percarbonate gives peracetic acid, the rate of peracetic acid formation was compared using composite TAED of the invention TAED form Ill in DES composite of the invention (TAED was 20% by total weight of composite. The DES is propylene glycol:citric acid in 1:1 molar ratio) and commercially available TAED.

Experimental Details

Part I

The experiments were carried out to check the performance and water miscibility of composite TAED of the invention in presence of sodium percarbonate. The TAED: Sodium percarbonate ratio used for the study was 1:2.5 w/w. Weighed amount of TAED (1 g of commercial sample and equivalent molar amount of composite TAED of the invention, i.e. 5 g) with sodium percarbonate was added to 100 ml water and stirred at 500 rpm using overhead stirrer. This 100 mL solution was either used as it was or it was further diluted to with 900 mL water to make a 1 L sample. The weight of the remaining material after 5 min was calculated. The samples were tested once stirring had stopped (T=0) and 6 months later ('T=6 months'; samples kept at 40° C. and 75% relative humidity) Results shows that TAED Form Ill shows complete miscibility or gives a clear solution as compared to marketed TAED (see Table below).

TABLE 4

| | Time Stirring | | | |
|---|---|---|---|---|
| | 1 min | | 4 min | |
| Experiment I (100 mL) | T = 0 | T = 6 months | T = 0 | T = 6 months |
| Undissolved TAED (Commercially available) | 150 mg (unclear solution) | 150 mg (unclear solution) | 100 mg (unclear solution) | 100 mg (unclear solution) |
| Undissolved composite TAED of the invention | 5 mg (clear solution) | 6 mg (clear solution) | 0 mg (clear solution) | 0 mg (clear solution) |

TABLE 4-continued

| | Time | | | |
|---|---|---|---|---|
| | 1 min | | 4 min | |
| Experiment II (1 L) | T = 0 | T = 6 months | T = 0 | T = 6 months |
| Undissolved TAED (Commercially available) | 90 mg (unclear solution) | 90 mg (unclear solution) | 60 mg (unclear solution) | 60 mg (unclear solution) |
| Undissolved composite TAED of the invention | 1 mg (clear solution) | 1.5 mg (clear solution) | 0 mg (clear solution) | 0 mg (clear solution) |

The above result shows that composite TAED of the invention dissolves in water in the presence of sodium percarbonate to a significantly greater extent than commercially available TAED.

Part II

Similar studies were carried out where TAED amount was increased to 3 gram (3 g of commercial sample and equivalent molar amount of composite TAED of the invention, i.e. 15 g) in 100 ml water. Results are shown in Table below

TABLE 5

| | Time Stirring | | | |
|---|---|---|---|---|
| | 1 min | | 4 min | |
| Experiment I (100 ml) | T = 0 | T = 6 month | T = 0 | T = 6 month |
| TAED (Commercially available) | 2 gram (unclear solution) | 2 gram (unclear solution | 1.8 gram (unclear solution) | 1.8 gram (unclear solution) |
| Undissolved composite TAED of the invention | 150 mg (almost clear solution) | 140 mg (almost clear solution) | 100 mg (almost clear solution) | 85 mg (almost clear solution) |
| | Time stirring | | | |
| | 1 min | | 4 min | |
| Experiment II (1 litre) | T = 0 | T = 6 month | T = 0 | T = 6 month |
| TAED (Commercially available) | 1.8 gram (unclear solution) | 1.8 gram (unclear solution) | 1.2 gram (unclear solution) | 1.2 gram (unclear solution) |
| Undissolved composite TAED of the invention | 90 mg (Visibly clear solution) | 80 mg (Visibly clear solution) | 25 mg (almost clear solution) | 23 mg (almost clear solution) |

The above result shows that composite TAED of the invention dissolves in water in the presence of sodium percarbonate to a significantly greater extent than commercially available TAED.

Example 5—Rate of Dissolution Procedure

The rate of dissolution of composite TAED form III in DES of the invention (TAED was 20% by total weight of composite. The DES is propylene glycol:citric acid in 1:1 molar ratio) in water (500 ml) was compared with the rate of dissolution of commercial tetraacetylethylenediamine (Form 1) at 20° C. using USP 11 dissolution apparatus. 1 g of commercial sample and the equivalent molar amount of composite TAED of the invention, i.e. 5 g. The powder of Examples 1 and 2 was spun from a disc at 50 rpm and samples taken at intervals of 5, 10, 15, 20 and 25 minutes. The amount of dissolved tetraacetylethylenediamine was monitored by high performance liquid chromatography. The results are shown in FIG. 3.

Figure 3:
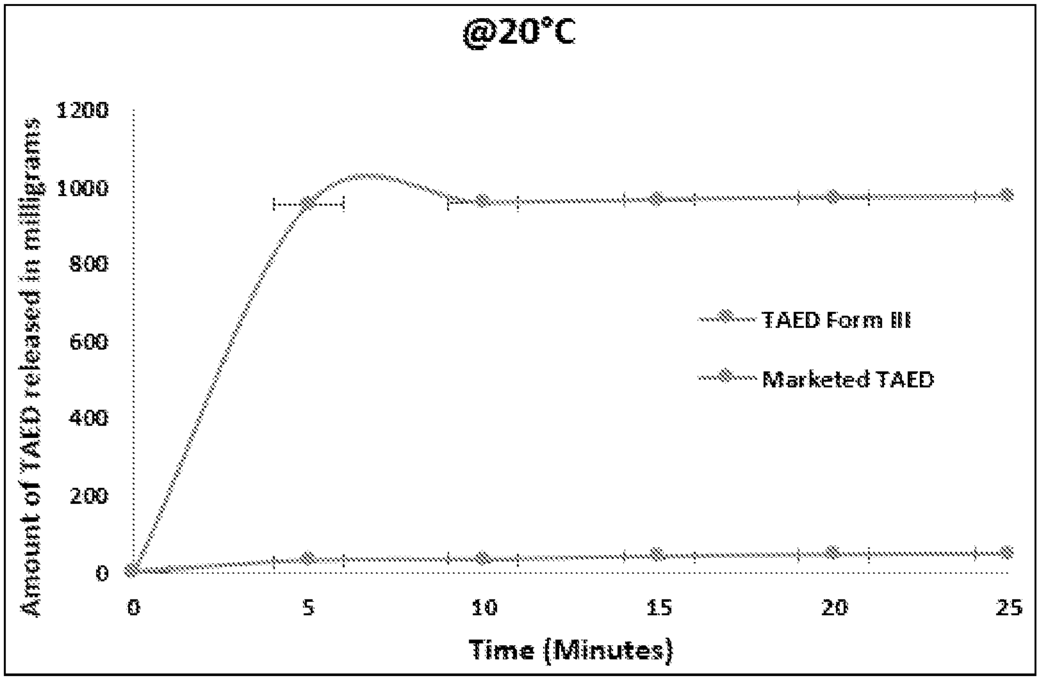
FIG. 3: Graph showing the rate of solution in water of composite TAED of the invention and TAED Form I.

FIG. 3 clearly shows that the rate of solution of composite TAED of the invention is more than 30 times faster than marketed TAED. This in turn will be reflected on the rate of peracetic acid generation. This clearly shows that composite TAED of the invention will generate peracetic acid at faster rate and that a more concentrated solution of peracetic acid can be prepared at 20° C.

Example 6—PAA Release

Four different samples of TAED in citric acid and propylene glycol (1:1 molar ratio) were prepared to assess whether the ratio of TAED to the DES has any influence on the rate of release of peracetic acid at room temperature (@20 C)

Sample 1 (liquid) TAED Concentration: 20-25% w/w of composite form

Sample 2 (liquid) TAED Concentration: 45-50% w/w of composite form

Sample 3 (semisolid) TAED Concentration: 60-65% w/w of composite form

Sample 4 (solid powder; also comprising a sodium lauryl sulfate like surfactant) TAED Concentration: 70-75% w/w relative to DES. The ratio of TAED/DES combination to surfactant was in the range 4:1 to 6:1

Analysis

The samples were mixed in water with sodium percarbonate (1:1.25). The samples were analyzed using a titration with 0.1 M potassium permanganate solution and 0.01M sodium thiosulphate solution. The samples were dissolved in 0.5 M sulfuric acid. After dissolving, potassium permanganate was added until colour change. During the addition, the pH and temperature of the sample were monitored to see if these parameters were changing during the titration. After the colour change, potassium iodide was added. By using a starch indicator solution the sample was titrated further with sodium thiosulphate until the colour change. The pH-value and temperature of the sample was also monitored during the titration.

The amounts of hydrogen peroxide was determined both samples using a titration with potassium permanganate. Sample 4 contains 203947 ppm hydrogen peroxide and sample 3 contains 141209 ppm hydrogen peroxide. Both samples were analysed in duplicate. Sample 1 contains 9380 ppm hydrogen peroxide. Sample 2010013597 contains 155462 ppm hydrogen peroxide. Determination of peracetic acid: titration with sodium thiosulphate Using a titration with sodium thiosulphate, the amount of peracetic acid in the samples was determined in duplicate. The results indicate that sample 4 contains 7599 ppm peracetic acid. Sample 3 contains 3178 ppm peracetic acid. Sample 1 contains 1387 ppm peracetic acid. Sample 2 contains 2452 ppm peracetic acid.

This shows that at 20° C., the composites of the invention offer very high levels of hydrogen peroxide and/or peracetic acid on exposure to percarbonate, even where very high loadings of TAED are used relative to the amount of DES. The solubility remains high, even with the solid sample 4.

The invention claimed is:

1. A composite form of tetraacetylethylenediamine (TAED), said composite form comprising TAED and an ionic component, wherein said ionic component is a Deep Eutectic Solvent (DES).

2. The composite form of claim 1, wherein the TAED is in a crystalline form (form III), said crystalline form being characterised in that said form has an XRPD pattern having only two peaks at 2θ 9.1746±0.2 and 18.1788±0.2 when the crystalline form is dispersed in the ionic component and wherein the XRPD is measured using Cu radiation with a $K_{\alpha2}/K_{\alpha1}$ ratio of 0.5.

3. The composite form of claim 1, wherein the composite form is a gel in which the TAED is the solid component and the ionic component is the liquid component.

4. The composite form of claim 1, wherein the composite form is a solid.

5. The composite form of claim 4 wherein the solid composite form further comprises a solid surfactant.

6. The composite form of claim 5, wherein the surfactant is selected from: Cresylic acid, Denatonium benzoate, Potassium peroxomonosulphate (KMPS), Glycollic acid, Sodium peroxodisulphate (NPS), Surface modifying polymers, Sodium sulphate, Zinc ricinoleate, Ethylene glycol distearate, Alkyl Polypentosides (APPs), Alkylpolyglucosides (APGs), Amine oxides, Amphoacetates, Cocamide DEA and MEA, Cocoaminopropionate, Cocoamphodipropionate, Cocoiminodipropionate, Didecyl dimethyl ammonium carbonate/bicarbonate, Dodecyl Benzene Sulfonic Acid (DDBSA), MEA & TEA neutralised DDBSA, Ethoxylated fatty amines, Fluorinated surfactants, Octyliminodipropionate, OXO alcohol ethoxylates, PEG-7 glyceryl cocoate, Propoxylate/Ethoxylates, Silicone surfactants, Sodium $C_{14-16}$ Olefin Sulphonate (AOS), Sodium $C_{14-17}$ Alkyl Sec-Sulphonate (SAS), Sodium Laureth Sulphate (SLES), Sodium Lauryl Sulphate (SLS), Urea and mixtures thereof.

7. The composite form of claim 4 wherein the composite form is a powder.

8. The composite form of claim 1, wherein the molar ratio of TAED to the ionic component is in the range 3:1 to 1:3.

9. The composite form of claim 1, wherein the DES is selected from choline chloride:lactic acid DES; proline: lactic acid DES; choline chloride:citric acid DES and propylene glycol:citric acid DES.

10. The composite form of claim 1, wherein the DES is propylene glycol:citric acid DES.

11. A method of forming a composite form of TAED, the method comprising:

a) heating TAED with deep eutectic solvent (DES) forming components, a DES solvent (DES), an Ionic liquid (IL) or a mixture thereof to a temperature≥150° C.; and b) allowing the mixture to cool to form the composite form of TAED.

12. The method of claim 11, wherein the eutectic solvent (DES) forming components, DES solvents (DES) or Ionic liquid (IL) are selected such that the product of step b) has a viscosity in the range from 5000 cP to 120000 cP.

13. The method of claim 11, wherein the heating step a) is optionally conducted in the presence of propylene glycol (1,2-Propylene Glycol), sodium tripolyphosphate, caustic soda, sulphonic acid, or mixtures thereof.

14. The method of claim 11, wherein the composite form formed in step b) is a gel and the method comprises step c): adding a solid surfactant to the product of b) to provide a composite form that is a solid.

15. The method of claim 14, wherein the solid surfactant is selected from: Cresylic acid, Denatonium benzoate, Potassium peroxomonosulphate (KMPS), Glycollic acid, Sodium peroxodisulphate (NPS), Surface modifying polymers, Sodium sulphate, Zinc ricinoleate, Ethylene glycol distearate, Alkyl Polypentosides (APPs), Alkylpolyglucosides (APGs), Amine oxides, Amphoacetates, Cocamide DEA and MEA, Cocoaminopropionate, Cocoamphodipropionate, Cocoiminodipropionate, Didecyl dimethyl ammonium carbonate/bicarbonate, Dodecyl Benzene Sulfonic Acid (DDBSA), MEA & TEA neutralised DDBSA, Ethoxylated fatty amines, Fluorinated surfactants, Octyliminodipropionate, OXO alcohol ethoxylates, PEG-7 glyceryl cocoate, Propoxylate/Ethoxylates, Silicone surfactants, Sodium $C_{14-16}$ Olefin Sulphonate (AOS), Sodium $C_{14-17}$ Alkyl Sec-Sulphonate (SAS), Sodium Laureth Sulphate (SLES), Sodium Lauryl Sulphate (SLS), Urea and mixtures thereof.

16. A composite form of TAED characterised in that it is obtainable by the method of claim 11.

17. A composition comprising the composite form of TAED of claim 1.

18. The composition of claim 17, wherein the composition is a solid composition.

19. The composition of claim 18, wherein the composition is a powder composition.

20. The composition of claim 17, wherein the composition comprises from 0.1% to 20% or 0.1 to 50% or more 75% by weight of the crystalline form of composite form of TAED.

21. The composition of claim 17, wherein the composition further comprises a bleaching agent.

22. The composition of claim 17, wherein the composition further comprises at least one of a surfactant or wetting agent.

23. The composition of claim 17, wherein the composition further comprises at least one of an additive selected from the group consisting of a pH modifier, a chelating agent, a stabilising agent, a diluent, a glidant, a binding agent, an effervescing agent, a disintegrating agent and a coating agent.

24. A crystalline form of TAED (form III), said crystalline form being characterised in that said form has an XRPD pattern having only two peaks at 2θ 9.1746±0.2 and 18.1788±0.2 when the crystalline form is dispersed in a DES solvent (DES), an Ionic liquid (IL) and wherein the XRPD is measured using Cu radiation with a $K_{\alpha 2}/K_{\alpha 1}$ ratio of 0.5.

* * * * *